United States Patent [19]
Breviglieri et al.

[11] Patent Number: 6,096,896
[45] Date of Patent: Aug. 1, 2000

[54] PROCESS FOR THE PREPARATION OF 4,5-DIPHENYLOXAZOLE-2-PROPANOIC ACID

[75] Inventors: Gabriele Breviglieri; Giacomo Bruno; Sergio Contrini; Cinzia Assanelli, all of Treviglio, Italy

[73] Assignee: Farchemia s.r.l., Treviglio, Italy

[21] Appl. No.: 09/172,476

[22] Filed: Oct. 15, 1998

[51] Int. Cl.[7] .................................................. C07D 263/30
[52] U.S. Cl. ............................................................ 548/236
[58] Field of Search ............................................... 548/236

[56] References Cited

U.S. PATENT DOCUMENTS 3,578,671  5/1971  Brown ...................................... 260/307
4,190,584  2/1980  Weston ..................................... 548/236

*Primary Examiner*—Mukund J. Shah
*Assistant Examiner*—Brenda Coleman
*Attorney, Agent, or Firm*—Nixon & Vanderhye P.C.

[57] ABSTRACT

In a process for the preparation of 4,5-diphenyloxazole-2-propanoic acid, the improvement consisting in using toluene in the esterification reaction of benzoin, and acetic acid/formic acid in the subsequent cyclization, thereby obtaining higher yields and avoiding the use and the disposal of high amounts of pyridine.

4 Claims, No Drawings

PROCESS FOR THE PREPARATION OF 4.5-DIPHENYLOXAZOLE-2-PROPANOIC ACID

The present invention relates to an improved process for the preparation of 4,5-diphenyloxazole-2-propanoic acid, of formula I

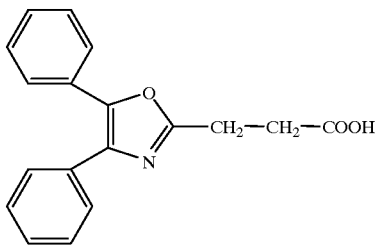

Compound I is a medicament with antiinflammatory activity (known under the non-proprietary name "oxaprozin"), that is prepared in two steps, by reaction of benzoin and succinic anhydride, and subsequent cyclization with ammonium acetate, as described in U.S. Pat. No. 3,578,671. More recent Patents, for example U.S. Pat. No. 4,190,584, claim the preparation of compound I in a single step, by acylation of benzoin with succinic anhydride in pyridine and direct cyclization of the intermediate benzoin hemisuccinate, without recovery, with ammonium acetate or urea.

This second process provides evident advantages compared with that described in U.S. Pat. No. 3,578,671, wherein the reaction between benzoin and succinic anhydride was carried out in the absence of a solvent and the resulting vitreous hemisuccinate intermediate was dissolved in ether, extracted in a $Na_2CO_3$ solution and—after washing the alkaline solution with ether—reprecipitated in oily form which subsequently solidified to give crystals.

The single-step process U.S. Pat. No. 4,190,584 provides a marked increase in yield compared with the prior art, in addition to a remarkable simplification in the operations.

It has now been found that the single-step process claimed by U.S. Pat. No. 4,190,584 can be further improved replacing pyridine with toluene, in the presence of catalytic amounts of 4-dimethylaminopyridine, and carrying out the cyclization with ammonium acetate or urea in a mixture of acetic acid and formic acid (in a ratio ranging from about 10:1 to about 5:1) instead of in only acetic acid.

4-Dimethylaminopyridine used as the catalyst is added in amounts ranging from 0.5 to 1.5% by weight compared with benzoin.

The advantages of the process according to the invention are the following ones. Operating in the best mode as, described in U.S. Pat. No. 4,190,584, about 58 kg of pyridine per 100 kg of resulting crude oxaprozin are necessary: pyridine not only cannot be recovered, but its disposal involves considerable problems. Although the process according to the present invention makes use of remarkably high amounts of toluene (about 450–550 liters, i.e. about 390–460 kg, per 100 kg of resulting pure oxaprozin), most toluene is easily recovered and recycled.

Furthermore, pyridine is known to be markedly more toxic than toluene. Moreover, according to Example 4 of U.S. Pat. No. 4,190,584, 100 kg of benzoin yield 73 kg of pure, first-crop oxaprozin, whereas operating according to the invention 100 kg of benzoin yield 94.8 kg of pure, first-crop oxaprozin. Apart from the recovers, the process yield herein claimed is 69.2%, while that of U.S. Pat. No. 4,190,584 is 61.4% totally.

The following example further illustrates the process according to the invention.

Example

A 2000 liter steel reactor is loaded with:

| | | |
|---|---|---|
| Succinic anhydride | Kg | 100 |
| Benzoin | Kg | 175 |
| 4-Dimethylamino pyridine | Kg | 1.7 |
| Toluene | L | 840 |

The mixture is blanketed with nitrogen and refluxed for 4 hours, then cooled to 40° C. and subjected to progressive vacuum to completely distil off toluene. 800 liters of toluene are recovered, which can be recycled. The residue is heated to 65° C. and added with:

| | | |
|---|---|---|
| acetic acid | L | 500 |
| formic acid | L | 83 |
| ammonium acetate | Kg | 133 |

The mixture is kept at 50° C. for 15', then heated at 105° C. for 6 hours under nitrogen stream, finally cooled to 80° C. and water L 292 is poured into the mixture, while heating the reactor to keep temperature at 80° C.

The product starts to crystallize. The mixture is maintained at 80° C. for 1 hour, then cooled at 0° C. for 2 hours. Crude oxaprozin is centrifuged and washed with 2×1000 liters of water and then with 75 liters of acetone. The humid product is placed in a 2000 liter steel reactor and added with:

acetone L 1200

The mixture is refluxed and filtered through a cartridge filter, washing the reactor and the filter with 50 liters of acetone. The filtrate is passed to a second reactor, which is the same as the first one, for further recovering.

The mixture is cooled to 45° C. and seeded with pure oxaprozin, leaving to crystallize at 45° C. for 1 hour, then cooling at 0° C. for 2 hours. The product is centrifuged, then washed while still in the centrifuge with 2×50 liters of acetone at 0° C. Drying in a static drier under vacuum yields Kg 166 of pure oxaprozin.

Similar results are obtained operating with urea instead of ammonium acetate.

What is claimed is:

1. A process for the preparation of 4,5-diphenyloxazole-2-propanoic acid of formula I

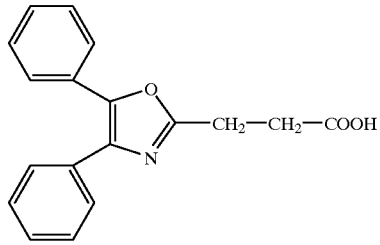

(I)

by esterification of benzoin with succinic anhydride to give benzoin hemisuccinate, and cyclization to (I) by direct addition of ammonium acetate or urea to the mixture containing the hemisuccinate, wherein in that the esterification reaction is carried out in toluene, with a catalytic amount of 4-dimethylaminopyridine, and wherein the cyclization is carried out in a mixture of acetic acid and formic acid.

2. A process as claimed in claim 1, in which toluene is used in a ratio of 450–550 liters per 100 kg of resulting pure oxaprozin.

3. A process according to claim 1, in which 4-dimethylaminopyridine is used in a 0.5–1.5% ratio by weight to benzoin.

4. A process according to claim 1, in which the cyclization is carried out in a mixture of acetic acid: formic acid in weight ratios ranging from about 10:1 to about 5:1.

* * * * *